United States Patent [19]

Woerner

[11] 4,020,180

[45] Apr. 26, 1977

[54] NONCORROSIVE CUPRAMMONIA FUNGICIDE AND METHOD FOR USING SAME

[75] Inventor: Hans Woerner, Mount Pleasant, N.C.

[73] Assignee: Mineral Research & Development Corporation, Charlotte, N.C.

[22] Filed: Aug. 11, 1975

[21] Appl. No.: 603,355

Related U.S. Application Data

[63] Continuation-in-part of Ser. No. 223,702, Feb. 4, 1972, Pat. No. 3,900,504.

[52] U.S. Cl. .......................... 424/294; 260/438.1; 424/166;311
[51] Int. Cl.$^2$ .......................................... A01N 9/00
[58] Field of Search ................ 260/438.1; 424/294, 424/166

[56] References Cited

UNITED STATES PATENTS

| | | | |
|---|---|---|---|
| 1,589,644 | 6/1926 | Hedenburg | 424/140 |
| 1,988,752 | 1/1935 | Sessions | 424/140 |
| 2,159,864 | 5/1939 | Serciron | 260/438.1 |
| 2,434,402 | 1/1948 | Fleer | 260/438.1 |
| 2,441,400 | 5/1948 | Doomani et al. | 260/438.1 |
| 2,444,945 | 7/1948 | Morrell | 260/438.1 X |
| 2,604,485 | 7/1952 | Booker et al. | 260/438 |
| 3,900,504 | 8/1975 | Woerner | 260/438.1 |

OTHER PUBLICATIONS

Chemical Abstracts 54:16247e.

Primary Examiner—Leonard Schenkman

[57] ABSTRACT

A substantially noncorrosive solution of cuprammonia low carboxylate complex of copper carboxylate and ammonium carboxylate is described wherein said complex is fungicidally and bactericidally effective when diluted with water in an amount of 3 to 200 parts of water per part of complex solution. The dilution effects the hydrolysis of the complex to precipitate in finely divided flocculent form fungicidally and bactericidally active copper values. When the flocculent precipitate is applied to the locus of bacteria or vegetation on which fungus is to be controlled, the flocculent precipitate forms a gelatinous coating of copper values which adhere tenaciously to the locus of application or vegetation where applied. Once dried, the coating adheres as a coating which is not readily removed by moisture or rainfall.

8 Claims, No Drawings

NONCORROSIVE CUPRAMMONIA FUNGICIDE AND METHOD FOR USING SAME

This is a continuation-in-part of Ser. No. 223,702 filed Feb. 4, 1972, now U.S. Pat. No. 3,900,504.

INTRODUCTION

This invention relates to divisible subject matter from the aforementioned parent application and more particularly relates to cuprammonia low carboxylate compositions which are substantially noncorrosive and which, when hydrolized, are bactericidally and fungicidally active, the hydrolized product formed therefrom, when applied to the locus of a fungus or bacteria to be controlled, effectively controls said fungus or bacteria.

BACKGROUND OF THE INVENTION

It is well-known that fungi are a large group of nongreen plants that receive their energy and raw materials through parasitic habits. Fungi are dependent upon the organic food made by photosynthesizing green plants. They represent a constant and ever present threat to many agricultural crops ranging from tropical and semi-tropical vegetation to temperate climate crops. The control of fungi has been achieved through the use of a heterogeneous group of chemicals termed "fungicides" that mitigate, inhibit or destroy fungi. Such fungicides have been applied by spray or dust applications of protective or eradicative amounts of the material to the locus of the fungi to be controlled.

The bacteria, also, form a well-known class of microscopic plants having round, rod-like, spiral or filamentous single-celled or non-cellular bodies which are often aggregated into colonies or motile by means of flagella. Bacteria live in soil, water, or organic matter, in the bodies of plants and animals, and are autotrophic, saprophytic, or parasitic in nutrition. Bacteria can be either helpful or harmful to mankind and are often used by man to his advantage. It is often desirable and necessary to control bacteria to prevent damage to organic matter. As such, bactericides perform a valuable function in the control or eradication of unwanted bacteria.

The compositions of this invention are particularly valuable as bactericides when applied to the locus of bacteria to be controlled in an effective amount. The method and amount of composition applied to effect bactericidal control is similar to the fungicidal method and amount. Consequently, the presented invention will be described more particularily with respect to the fungicidal use because such use has been more extensively investigated and is the preferred use. This, however, is not to in any manner limit the scope of the present invention, but rather is a manner of more clearly setting forth the preferred embodiments of the present invention.

Prior to about 1939, inorganic sulfur and copper compounds were used almost exclusively as sprays and dust fungicides. Copper and mercury compounds were also used as applications in seed treatments. As early as 1882, copper sprays were introduced as a Bordeaux mixture for the control of downy mildew on grapes. The Bordeaux mixture consisted of a light blue gelatinous precipitate suspended in water and formed by reacting 4 parts of copper sulfate to 4 parts of hydrated lime (calcium hydroxide) in 50 gallons of water. Various variations in the composition of the resulting mixture have been made by changing the ratio of the components.

While copper compounds have been known for their ability to control fungi, soluble copper compounds are known to be extremely toxic to vegetation. Consequently, the copper materials applied must be relatively non-toxic to the plants while being effective fungicides. As such, it is necessary, in order to have an effective fungicide, to have an insoluble copper material in finely divided form which can be effectively applied to vegetation in a manner whereby it will adhere to the vegetation while remaining non-toxic to the vegetation to which it is applied. The finer the copper compound, the more surface area it can cover and therefore, in general, the more effective it will be per unit weight.

It is well-known that various materials, including copper compounds, can be milled to extremely fine particle size such that the surface area of the particle becomes extremely large. With finely milled material, theoretically such material is able to cover massive surface areas with relatively small amounts of copper compound. As a practical matter, it is extremely difficult to disperse and/or redisperse such finely milled copper materials because of the tendency of fine particles to agglomerate such that the finely divided particles are not fully dispersed but rather accumulate as larger particles, thus greatly reducing the effectiveness and surface area of the material.

It has been discovered that an effective way of producing the required finely divided dispersant of copper values is to precipitate the copper values in situ. Under certain desirable conditions, copper can be made to precipitate in the desired finely divided state. However, it is also well-known that the more desirable copper solutions are corrosive, particularly visa brass. For example, copper chloride is used as an etchant. Cuprammonia is known to be a much more powerful corrosive than either copper or ammonium ions individually. With the corrosive nature of copper solutions, it is particularly parenthetical that brass is the most widely used material for fungicidal spraying equipment, particularly the pumps, valves and nozzles used in such equipment. This corrosiveness is well documented by Rumford, *Chemical Engineering Materials*, 1st American Edition, pp. 194.

If the ammonia in a spray-type cuprammonia fungicide solution is bound by simply changing the pH, then as the pH of 7 is approached on the alkaline side, the copper quantitatively turns to an insoluble form which settles to the bottom of the storage containers. On the other hand, if the copper is prevented from precipitating with chelating agents such as EDTA (ethylene diamino tetra acetate), it will not deposit the active adherent form of copper required to protect the vegetation.

It is, therefore, an object of the present invention to provide a cuprammonia low carboxylate solution which is substantially noncorrosive to metal surfaces.

It is another object of the present invention to provide a cuprammonia low carboxylate solution which is readily hydrolizable to insoluble copper form which is fungicidally active.

It is another object of the present invention to provide a cuprammonia low carboxylate material which, on hydrolysis, forms a finely divided flocculent precipitate of copper values which, when applied to vegetation, forms a gelatinous coating which adheres tenaciously to the vegetation.

It is yet a further object of the present invention to provide an effective fungicidal composition which comprises finely divided copper values which are not readily removed by the subsequent application of moisture such as dew or rainfall.

These and other objects of the present invention will become readily apparent from the description of the invention which follows.

THE INVENTION

In accordance with the invention, there is provided a substantially noncorrosive solution which is dilutable to a fungicidal composition comprising a cuprammonia low carboxylate complex of copper carboxylate and ammonium carboxylate, said complex being in a dilute ammonium solution at a pH in the range of about 7.1 to 7.4, said solution having a copper content of about 8 to 8.2 percent by weight.

The low carboxylate is selected from the group consisting of formate, acetate and propionate, with acetate being the most preferred carboxylate.

The present composition effectively eliminates, suppresses, retards, reduces, or otherwise controls the activity of a wide variety of fungi and bacteria.

The composition can be applied as a dilute spray or concentrate spray either in ground applications or aerial applications. The composition can be used alone or in conjunction with insecticides, miticides, or other fungicides as well as extenders, surfactants, spreaders, stickers, or oils including colloidal and non-ionic materials.

DETAILS OF THE INVENTION

The composition of the present invention is produced by reacting specific amounts of copper, ammonium low carboxylate, and aqueous (29%) ammonia so as to produce a complex having a pH in the range of about 7.1 to about 7.4 and a copper content of about 8.0 to approximately 8.20 percent. In place of acetate, the corresponding formate or propionate can be substituted in corresponding proportions to produce a complex of comparable copper content and pH range. Because the most preferred carboxylate is acetate, the invention will be more fully described with reference to acetate, while it should be recognized that formate and/or propionate can be substituted for the acetate in similar proportions to produce correspondingly good results. Consequently, because the preferred mode of invention is with acetate, the description will be described hereinafter more particularly with respect to the acetate embodiment.

The composition of the present invention can be produced by several methods. One method is the utilization of metallic copper, ammonium hydroxide, or anhydrous ammonia, acetic acid and water reacted at a basic pH at elevated temperatures with the addition of oxygen or air. The complex can be produced by reacting the prerequisite amounts of copper, and ammonia and acetic acid below reflux at a pH in excess of 7 and preferably 8 or more, subsequently adjusting the pH to the desired range of 7.1 to 7.4 by raising temperature to reflux and evaporating ammonia from the reaction solution. Alternatively, rather than using mettalic copper, copper oxide can be substituted.

This latter method is not as suitable for the production of the corresponding propionate complex because copper oxide tends to form upon refluxing of such complex. The noted method, however, is quite acceptable and desirable for the production of either the corresponding formate or acetate complex.

Alternatively, a particularly desirable method of forming the complex is by direct reaction of copper acetate, ammonium acetate in aqueous ammonia. Typically, 132 parts of copper acetate in the dehydrate form are reacted in a solution of 220 parts water and 100 parts of aqueous ammonia (29% $NH_3$) and 20 parts of ammonium acetate. The resulting mixture is reacted at room temperature up to the reflux temperature to produce a cuprammonia acetate complex having a pH in the range of 7.1 to 7.4 and a copper content of about 8.0 to 8.2 percent.

The resulting preferred complex has a specific gravity within the range of 1.155 to 1.166, the variability being dictated by the exact amount of copper values and the inerts which might be present.

It should be noted that acetic acid or acetates in conjunction with copper are not ordinarily considered solublizing (chelating) agents for copper. To the contrary, the presence of acetic acid or acetates is considered to lower the solubility of copper salts. Illustratively, the nitrates, chlorides, and sulfates of copper all have solubilities several times that of copper acetate. In addition to making copper soluble at pH conditions where it would normally be precipitated, the reaction product retains the desired precipitate characteristics found in cuprammonia complexes. This is accomplished by depositing a hydroxide form of copper rather than a basic acetate when the copper acetate solution is diluted.

Attempts to structurally determine the reaction products of the present invention by the usual analytic chemical techniques of functional group analysis, degradative structural analysis and the separation and identification of residues has been inconclusive. It is believed that the reaction product is a cuprammonia acetate complex having the mono-molecular form $Cu(NH_3)_2$ $(O-CO.CH_3)_2$. While applicant does not wish to be bound by any particular theory, it is believed that the composition is best identified by the proportions of copper, ammonia, acetate and pH of the solution.

The complex of the present invention is considered to be a concentrate which retains its clear solution characteristics.

For fungicidal or bactericidal used, the complex of the present invention is hydrolized by diluting the complex with water in the amount of about 3 to 200 parts of water per part of complex solution. The water dilution hydrolizes the complex, thereby forming a copper hydroxide precipitate which has the particularly desirable property of forming a finely dispersed flocculent material which remains suspended in solution with a very slow settling tendency. This flocculent precipitate of finely divided copper values is readily applied to the locus of fungi or bacteria to be controlled such as by spraying the area to be treated. The applied hydrolized precipitate forms a tough gelatinous film on vegetation, plants, leaves, etc. Once this film dries, it adheres tenaciously to the substrate to which is was applied and is not readily removed by the action of rain, dew, or other atmospheric moisture.

The gelatinous nature of this hydrolized complex makes it particularly useful in conjunction with other chemicals which otherwise do not readily lend themselves to durable applications to vegetation. For instance, materials of low water solubility such as sulfur and lime can be made to adhere to vegetation in dispersed form by the binding effect of the present material.

The composition of the present invention can additionally be mixed with various other fungicidal, herbicidal, insecticidal, bactericidal, or inert materials which are desirably applied along with the present material. For instance, finely divided sulfur, lime, fillers, or inerts can be mixed with the present composition. Further, various other fungicides form compatible mixtures and/or synergists with the present composition.

It is frequently desirable to add insecticides, miticides, or herbicides in the same spraying application. Such compositions, for the most part, are compatible with the present composition. Typical examples of such materials which can be mixed and applied with the present invention include chlorobenzilates, and composition sold under the trade names of Benlate 50W; Bravo W-75; Captan 50-W; Cygon 267; Diazinon; Difolatan 4 Flowable; DiSyston 4EC; Dithane M-45; Dursban Insecticide; Ethion 4E; Guthion; Kelthane MF; Lannate-L; Malathion EC; Manzate 200; Methyl & Ethyl Parathion EC; Phosdrin 4 ED, Plictran Miticide; Sevimol 4; Sevin 80 WP; Systox; Thiodan; Topsin-M; Toxaphene; Trithion 4E; and many others.

Most non-ionic and/or colloidal surfactants, spreaders, and stickers can also be used with the present composition. Such materials are often useful in aiding the dispersal of otherwise difficult to disperse additives which might be desirably mixed with the present invention in simultaneous applications.

The rate of application depends upon the particular plant being treated and the fungus against which protection is desired. The concentrate is preferably diluted in the amount of 3 to 100 parts of water per part of complex. The dilution product is applied in the amount of 2 to about 800 gallons of water per acre.

Typical of the fungus which can be controlled by the present invention when applied to the locus of the fungus to be controlled include almond brown rot, apricot brown rot, blossom rot, beans bacterial blight and halo blight, carrots early and late blight, celery early and late blight, citrus fruits melanose and greasy spot; cantaloupes, melons, cucumbers, squash, etc. powdery mildew, scab, Alternaria and angular leaf spots, coffee beans, grapes anthracnose, peanuts cercospora leaf spot, peaches and nectarines blossom rot, peppers cercospora leaf spot and bacteria spot, potatoes early and late blight, strawberries leaf spot and scorch, sugar beets cercospora leaf spot, tomatoes early and late blight and bacterial spot, walnut blight and numerous other fungus and other fungus and bacteria.

The invention will be more readily understood by reference to the following example which illustrates certain preferred embodiments of the present invention and in no way are to be taken as limiting the scope of the present invention. Unless otherwise noted, all parts and percentages are by weight.

EXAMPLE 1

In this experiment, cuprammonia acetate and cuprammonia carbonate were diluted and the amount of copper precipitate was measured. This illustrates the deposition control property of the composition according to this invention. At the end of this time period, the copper content in terms of the grams copper per liter left in solution and the percent copper precipitated were measured for each dilution ratio.

| Cuprammonia Acetate Complex 8% Cu | | | | | |
|---|---|---|---|---|---|
| Dilution | 3:1 | 6:1 | 30:1 | 60:1 | 100:1 |
| Gr Cu/Liter left in sol. | 16.15 | 6.78 | 0.40 | 0.15 | 0.038 |
| % Cu precipitated | 30.39 | 48.91 | 86.67 | 90.14 | 95.86 |

| Copper Ammonia Carbonate 8% Cu | | | | | |
|---|---|---|---|---|---|
| Dilution | 3:1 | 6:1 | 30:1 | 60:1 | 100:1 |
| Gr Cu/Liter left in sol. | 23.76 | 13.10 | 2.976 | 1.296 | 0.54 |
| % Cu precipitated | 1.02 | 4.59 | 4.00 | 17.45 | 43.16 |

EXAMPLE 2

Two identical brass surfaces were exposed at least 48 hours in respective solutions of cuprammonia acetate and cuprammonia carbonate. The object of this test was to determine the difference, if any, in the corrosion rates of the brass as a function of exposure to these solutions.

It was observed that the corrosion rate of brass exposed to the acetate in terms of weight loss after 48 hours, was 0.582 grams or an absolute rate of 0.0102 inches per month. In contrast, the carbonate caused a brass weight loss of 13.61 grams at an absolute rate of 0.2417 inches per month.

EXAMPLE 3

The composition of the present invention was produced by reacting at atmospheric temperature pressure about 13 parts of copper acetate dihydrate with about 2 parts of ammonium acetate in a solution of 10 parts of 29 percent aqueous ammonia and about 22 parts of water. On mixing and reacting, a slight exothermic reaction was noted. The pH of the solution was adjusted to be within the range of 7.1 to 7.4 and the copper content in the range of 8.0 to 8.2 percent.

EXAMPLE 4

In the same manner, copper ammonium formate was reacted at atmospheric temperature and pressure using the same molar proportions as Example 3, but substituting ammonium formate for the ammonium acetate and cooper formate for copper acetate. On reacting, a slight exothermic reaction was also noted. The resulting cuprammonium formate complex was adjusted to a pH between 7.1 and 7.4 in a copper content of 8.0 to 8.2 percent.

EXAMPLE 5

In the manner of Example 3, copper ammonium propionate complex was produced by reacting copper propionate at room temperature and pressure with ammonium propionate in aqueous solution with ammonia in the molar proportions of Example 3. A slight exothermic reaction was noted on mixing and reacting. The resulting cuprammonium propionate complex was adjusted to a pH between 7.1 and 7.4 in a copper content of 8.0 to 8.2.

EXAMPLE 6

Cuprammonium acetate complex of the present invention was prepared by reacting metallic copper and oxygen or air in a solution of ammonium hydroxide and acetic acid. An aqueous solution of about equal molar proportions of acetic acid and ammonium hydroxide was prepared and the pH of the solution was adjusted to between 8 and 12 by the addition of excess ammonium hydroxide. Finely divided copper was then added to equal about 8.0 to 8.2 percent by weight.

Oxygen (air) was bubbled through the solution. An exothermic reaction was noted. The pH of the complex solution was then adjusted to between 7.1 and 7.4 by evaporating ammonia from the complex solution.

In the same manner, anhydrous ammonia can be substituted for all or part of the ammonium hydroxide and copper oxide of metallic copper and air in place of oxygen with correspondingly good results.

EXAMPLE 7

The composition of the present invention as described more particularly in Example 3 was tested for fungicidal and bactericidal activity by treating various crops with the complex diluted with water as set forth in Table I.

Table I

| Plant | Fungus to be Controlled | Amount of Application | % Foliar Infection of Treated | % Foliar Infection of Nontreated | Increased Yield |
|---|---|---|---|---|---|
| Head Lettuce | Downy Mildew | 1 pt/A in 25 gal H$_2$O | 9.0 | 28.7 | |
| Cabbage | Downy Mildew | 1 pt/A in 25 gal H$_2$O | 6.5 | 27.6 | |
| Cauliflower | | | 7.7 | 29.1 | |
| Cabbage | Altervaria Blight | 1 pt/A in 25 gal H$_2$O | 18.8 | 37.8 | |
| Cauliflower | Altervaria Blight | 1 pt/A in 25 gal H$_2$O | 11.3 | 28.9 | |
| Soybean | Fungus - Various | ⅔ gal/A in 50 gal H$_2$O | — | — | 8% |
| Onions | Rot Control of Dried Onions | 3.3 qt/ 100 gal H$_2$O as a dip | 25.0 | 61.5 | |
| Pecan | Scab | 3 qts/ 100 gal | — | — | 48% |

The above examples illustrate but a few of the fungi controlled by the composition of the present invention when applied to the locus of the fungus to be controlled. The test results indicate that substantial benefits are obtained in reducing the fungicidal activity as measured by reduction in infected foilage or increased yield as compared to the control which was untreated plants.

While the invention has been described with reference to particular preferred embodiments thereof, it will be understood by those skilled in the art that various changes in form and detail may be made therein without departing from the spirit or scope of the invention. Consequently, the invention is not to be limited other than as set forth in the appended claims.

What is claimed is:

1. A substantially noncorrosive aqueous concentrate solution which is dilutable with water to a fungicide composition comprising an aqueous cuprammonium lower carboxylate complex of copper lower carboxylate and ammonium lower carboxylate in weight proportions of about 13 parts of copper lower carboxylate as measured as the dihydrate to about 2 parts of ammonium lower carboxylate, and about 10 parts of 29 percent aqueous ammonia, said solution being at a pH in the range of about 7.1 to 7.4.

2. The solution of claim 1 wherein the carboxylate of the complex is selected from the group consisting of formate, acetate, propionate and mixtures thereof.

3. The solution of claim 1 wherein the carboxylate of the complex is acetate.

4. The solution of claim 3 wherein the specific gravity is between 1.155 to 1.166.

5. The solution of claim 3 wherein the concentrate solution is diluted with water to a copper content of about 8 to 8.2 percent by weight.

6. A fungicidal composition containing about 3 to 200 parts of water to 1 part of the solution of claim 3, said water being present in an amount sufficient to hydrolyze the complex and to precipitate copper values from the solution.

7. A fungicidal composition containing about 3 to 200 parts of water to 1 part of the solution of claim 1, said water being present in an amount sufficient to hydrolyze the complex.

8. A method of controlling fungi and bacteria on crops which comprises applying to the loci thereof a fungicidally or bactericidally effective amount of the solution of claim 7.

* * * * *